US012558110B2

(12) United States Patent

Kollmeier et al.

(10) Patent No.: US 12,558,110 B2

(45) Date of Patent: Feb. 24, 2026

(54) SCREW-THROUGH ACETABULAR CUP SYSTEM AND METHODS OF USING THE SAME

(71) Applicant: Howmedica Osteonics Corp., Mahwah, NJ (US)

(72) Inventors: Morgan Kollmeier, Ridgewood, NJ (US); Robert Davignon, Denville, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 696 days.

(21) Appl. No.: 18/080,142

(22) Filed: Dec. 13, 2022

(65) Prior Publication Data

US 2023/0190313 A1 Jun. 22, 2023

Related U.S. Application Data

(60) Provisional application No. 63/292,754, filed on Dec. 22, 2021.

(51) Int. Cl.
| | |
|---|---|
| *A61F 2/46* | (2006.01) |
| *A61B 17/17* | (2006.01) |
| *A61F 2/34* | (2006.01) |

(52) U.S. Cl.
CPC ........ *A61B 17/1746* (2013.01); *A61F 2/4609* (2013.01); *A61F 2002/3403* (2013.01); *A61F 2002/3483* (2013.01)

(58) Field of Classification Search
CPC ............ A61F 2/4684; A61F 2002/4687; A61F 2/4609; A61F 2002/3401; A61F 2002/3448; A61F 2002/30607; A61F 2002/30614; A61F 2002/30616; A61B 17/1746
See application file for complete search history.

(56) References Cited

U.S. PATENT DOCUMENTS

| | | | | | |
|---|---|---|---|---|---|
| 5,879,401 | A | * | 3/1999 | Besemer | A61F 2/4684 |
| | | | | | 623/22.28 |
| 6,416,553 | B1 | * | 7/2002 | White | A61F 2/4637 |
| | | | | | 623/22.38 |

(Continued)

FOREIGN PATENT DOCUMENTS

| | | | | | |
|---|---|---|---|---|---|
| CA | 2815654 | C | * | 2/2019 | ........... A61F 2/4609 |
| CN | 114145808 | A | * | 3/2022 | ......... A61B 17/1659 |

(Continued)

*Primary Examiner* — Alvin J Stewart
(74) *Attorney, Agent, or Firm* — Lerner David LLP

(57) ABSTRACT

A surgical guide system includes a shell trial having a convex side configured to engage an acetabulum, a concave side forming a cavity therein, and windows extending through the convex and concave sides for viewing bone. The system further includes a liner trial having a convex side configured to be received within the cavity of the concave side of the shell trial, and a concave side with recessed hole guides there, wherein more than one of the hole guides align with the windows of the shell trial when the liner trial is received therein. The system further includes an acetabular cup implant having a convex side configured to engage an acetabulum, a concave side, and a thickness extending between the concave and convex sides, the concave side defining a cavity configured to receive the liner trial.

20 Claims, 8 Drawing Sheets

(56) References Cited

U.S. PATENT DOCUMENTS

| | | | | |
|---|---|---|---|---|
| 6,527,809 B1 * | 3/2003 | Doursounian | A61F 2/34 | 623/22.25 |
| 7,537,664 B2 | 5/2009 | O'Neill et al. | | |
| 8,585,769 B2 * | 11/2013 | Vankoski | A61F 2/4684 | 623/22.24 |
| 8,728,387 B2 | 5/2014 | Jones et al. | | |
| 9,180,010 B2 | 11/2015 | Dong et al. | | |
| 9,456,901 B2 | 10/2016 | Jones et al. | | |
| 9,526,514 B2 * | 12/2016 | Kelley | A61B 17/15 | |
| 9,956,089 B2 * | 5/2018 | Kelman | A61F 2/4609 | |
| 10,568,746 B2 * | 2/2020 | Kelman | A61F 2/4609 | |
| 10,716,677 B2 * | 7/2020 | Lewallen | A61F 2/34 | |
| 10,729,558 B2 * | 8/2020 | Macke | A61B 34/10 | |
| 11,298,189 B2 * | 4/2022 | Kelman | A61B 34/10 | |
| 11,801,151 B2 * | 10/2023 | Wilkins | A61F 2/4609 | |
| 12,144,747 B2 * | 11/2024 | Loiacono | A61F 2/34 | |
| 2005/0021148 A1 * | 1/2005 | Gibbs | A61F 2/30734 | 606/86 R |
| 2006/0058886 A1 * | 3/2006 | Wozencroft | A61F 2/4609 | 606/91 |
| 2006/0147332 A1 | 7/2006 | Jones et al. | | |
| 2006/0190089 A1 * | 8/2006 | Montoya | A61F 2/34 | 623/22.32 |
| 2009/0216332 A1 * | 8/2009 | Splieth | A61F 2/4684 | 623/19.14 |
| 2011/0009975 A1 * | 1/2011 | Allen | A61F 2/4684 | 623/22.24 |
| 2012/0016486 A1 * | 1/2012 | Yokoo | A61F 2/30771 | 623/22.24 |
| 2012/0150311 A1 * | 6/2012 | Meridew | A61F 2/30734 | 623/22.25 |
| 2012/0185059 A1 * | 7/2012 | Vankoski | A61F 2/4684 | 623/22.24 |
| 2013/0041474 A1 * | 2/2013 | Davenport | A61F 2/30744 | 623/22.34 |
| 2013/0310946 A1 * | 11/2013 | Sun | A61F 2/34 | 623/22.38 |
| 2014/0039638 A1 * | 2/2014 | Meridew | A61F 2/34 | 623/22.28 |
| 2014/0074249 A1 * | 3/2014 | Davenport | A61F 2/4609 | 623/22.24 |
| 2014/0100579 A1 * | 4/2014 | Kelman | A61F 2/4609 | 606/91 |
| 2014/0114429 A1 * | 4/2014 | Slone | A61F 2/34 | 623/22.34 |
| 2014/0249535 A1 * | 9/2014 | McCarthy | A61F 2/4684 | 606/91 |
| 2014/0303742 A1 * | 10/2014 | Prybyla | A61F 2/3662 | 623/22.19 |
| 2015/0250620 A1 * | 9/2015 | Brown | A61F 2/4684 | 623/22.15 |
| 2016/0089156 A1 * | 3/2016 | Fortin | A61B 17/1617 | 606/81 |
| 2017/0065420 A1 * | 3/2017 | Sartawi | A61F 2/4609 | |
| 2018/0036129 A1 * | 2/2018 | Mistry | A61F 2/30734 | |
| 2018/0214233 A1 * | 8/2018 | Termanini | A61F 2/4637 | |
| 2018/0353305 A1 * | 12/2018 | Bushell | A61F 2/468 | |
| 2019/0053915 A1 * | 2/2019 | Macke | A61F 2/34 | |
| 2019/0254827 A1 * | 8/2019 | Rister | A61F 2/4684 | |
| 2020/0038190 A1 * | 2/2020 | McCleary | A61F 2/30734 | |
| 2020/0261248 A1 * | 8/2020 | Wills | A61F 2/4684 | |
| 2020/0289292 A1 * | 9/2020 | Wilkins | A61F 2/34 | |
| 2021/0154016 A1 * | 5/2021 | Albert | A61F 2/34 | |
| 2022/0000641 A1 * | 1/2022 | Wills | A61F 2/4684 | |
| 2022/0151792 A1 * | 5/2022 | Lee | A61F 2/34 | |
| 2022/0233318 A1 * | 7/2022 | Zhang | A61F 2/32 | |
| 2022/0249254 A1 * | 8/2022 | Loiacono | A61F 2/3609 | |
| 2023/0363918 A1 * | 11/2023 | Hudson | A61F 2/34 | |
| 2024/0335291 A1 * | 10/2024 | Haggerty | A61F 2/30771 | |
| 2024/0374391 A1 * | 11/2024 | Stumpo | A61F 2/34 | |

FOREIGN PATENT DOCUMENTS

| | | | | | |
|---|---|---|---|---|---|
| EP | | 1082949 A1 * | 3/2001 | | A61F 2/34 |
| FR | | 2785522 A1 * | 5/2000 | | A61B 17/8605 |
| WO | WO-2011156508 A2 * | | 12/2011 | | A61F 2/30749 |
| WO | WO-2019038032 A1 * | | 2/2019 | | A61F 2/4684 |
| WO | WO-2022117949 A1 * | | 6/2022 | | A61F 2/4684 |
| WO | WO-2025046260 A1 * | | 3/2025 | | A61B 17/1746 |

* cited by examiner

SCREW-THROUGH ACETABULAR CUP SYSTEM AND METHODS OF USING THE SAME

CROSS-REFERENCE TO RELATED APPLICATIONS

This application claims the benefit of the filing date of U.S. Provisional Patent Application No. 63/292,754 filed Dec. 22, 2021, the disclosure of which is hereby incorporated herein by reference.

BACKGROUND OF THE INVENTION

Joint arthroplasty procedures involve the replacement of a natural joint surface with an artificial joint surface. Many articulating joints of the body, such as the joints of the hips, have anatomical ball and socket connections between bones of the joints providing a wide range of motion. The hip joint, for instance, includes a socket or acetabulum in the pelvis and a femoral head or ball at an upper end of the femur or thigh bone received in the acetabulum. When natural articulating joints degrade or become defective due to disease or injury, prosthetic or artificial ball and socket components may be surgically implanted into the body to replace the natural ball and socket structure of the joints. One approach to hip replacement surgery involves the use of an acetabular cup which is located within the acetabulum of the pelvis. The acetabular cup provides a prosthetic articulating surface against which an articulating surface of the femoral head, or a prosthetic femoral head, can bear in use.

Acetabular cups are typically secured to underlying bone via bone cement or press-fit fixation. Acetabular cups that are press-fit commonly include a porous bone interfacing structure that promotes bone ingrowth for long-term fixation. However, since it ordinarily takes time for bone to grow into the porous structure, secondary means of fixation, such as bone screws, are often utilized to help secure the acetabular cup while ingrowth takes place.

Prior to securing the acetabular cup to the underlying bone, it is crucial to ensure correct positioning of the acetabular cup prosthesis. Just as the natural hip wears with time, the prosthesis will also wear with time. However, if the acetabular cup prosthesis is not correctly seated in the acetabulum, the wear rate of the of the prosthetic implant may be higher than when the prosthetic implant is in the optimal position. Moreover, incorrectly positioned acetabular cups can cause abnormal gait, patient discomfort, and/or impingement limiting the artificial joint's range of motion.

The correct positioning of an acetabular cup prosthesis can be complicated by underlying bone that is weakened in certain areas due to damage or disease, such as osteolysis and the like, such that the bone is not adequate to support the secondary means of fixation. Visual inspection can help distinguish regions of healthy bone from those of unhealthy bone so that the operator can utilize the healthy bone to secure the prosthesis thereto. However, currently existing surgical instruments and implants often obscure the underlying bone making it difficult to determine whether the means for fixing the trial cup or the prosthesis to the bone has adequate support prior to the deployment of the same.

Currently available acetabular cup prostheses provide an overabundance of screw holes in an effort to ensure that at least one or some of those screw holes will align with dense, healthy bone when the cup is properly positioned. However, this overabundance of screw holes, many of which are not utilized, minimizes the porous structure available for bony ingrowth. Thus, further improvements are desirable.

BRIEF SUMMARY OF THE INVENTION

In one aspect of the present disclosure, a surgical guide system includes a shell trial having a convex side configured to engage an acetabulum, a concave side forming a cavity therein, and windows extending through the convex and concave sides for viewing bone. The system further includes a liner trial having a convex side configured to be received within the cavity of the concave side of the shell trial, and a concave side with recessed hole guides there, wherein more than one of the hole guides align with the windows of the shell trial when the liner trial is received therein. The system further includes an acetabular cup implant having a convex side configured to engage an acetabulum, a concave side, and a thickness extending between the concave and convex sides, the concave side defining a cavity configured to receive the liner trial. The concave side also has a plurality of holes extending therein and at least partially into the thickness, wherein the recessed hole guides and holes of the acetabular cup align when the liner trial is received within the cavity of the acetabular cup implant.

Additionally, the recessed hole guides of the liner trial may be located adjacent one another and arrayed about a polar axis of the liner trial.

Furthermore, the plurality of holes in the acetabular cup may be positioned adjacent one another and arrayed about a polar axis of the acetabular cup.

Additionally, the acetabular cup may include a rim defined by a convergence of the concave and convex sides thereof and the rim may include a first engagement feature. The liner trial may include a rim defined by a convergence of the concave and convex sides thereof and the rim may include a second engagement feature. The recessed hole guides of the liner trail may align with the plurality of holes in the acetabular cup when the first and second engagement features engage with each other.

Additionally, the surgical guide system may include a vice having a concave cavity for receiving the acetabular cup implant and it may have a plurality of cylindrical or conical channels in communication with the concave cavity. The cylindrical or conical channels may align with the plurality of holes of the acetabular when they are received within the concave cavity.

Furthermore, the acetabular cup implant may have a porous structure on the convex side such that the porous structure occludes the plurality of holes.

Additionally, the convex side of the acetabular cup implant is formed from a solid material which defines each of the plurality of holes in the acetabular cup implant. The material may be metal.

In another aspect of the present disclosure, a liner trial for visualizing the placement of a bone screw includes a convex bone facing side and a concave visualization side opposite the bone facing side. A thickness is defined between the bone facing side and visualization side. The liner trial also includes hole guides extending radially outwardly into the visualization side and partially into the thickness.

Additionally, the liner trial may be transparent.

Furthermore, the hole guides of the liner trial may be spaced adjacent one another to cover a maximum amount of surface area on the concave visualization side.

Additionally, the liner trial may include an insertion feature having a threaded bore. The threaded bore may correspond to a threaded portion of an attachment feature.

Additionally, the attachment feature may at least one of a window trial, vice, and implant.

Additionally, the liner trial may be disposable.

In another embodiment, the insertion feature may frictionally engage with at least one of a window trial, vice, and implant.

In a further aspect of the present disclosure, a method of implanting a prosthesis into a bone cavity includes inserting a window trial with a first window into a bone. The method further includes placing a guide trial with a first hole guide into the window trial, drilling through the first hole guide and the first window into the bone, and removing the guide trial from the bone. Next, the method includes placing the guide trial into a prosthesis, the prosthesis having an inner surface with a plurality of holes and a porous outer surface occluding the holes. Next, the method includes drilling through the first guide hole, a first hole of the plurality of holes in the inner surface of the prosthesis, and the porous outer surface, inserting the prosthesis into bone, and inserting a bone screw through the first hole in the prosthesis and into the bone.

Additionally, the bone structure may be an acetabulum.

Additionally, the method may further include aligning the first window of the window trial with a region of relatively dense bone.

Furthermore, the guide trial may be transparent.

Additionally, the method may further include drilling through a second hole guide and second window into the bone, drilling through the second guide hole, a second hole of the plurality of holes in the inner surface of the prosthesis and the porous outer surface, and inserting a bone screw through the second hole in the prosthesis and into the bone.

Additionally, placing the guide trial into the window trial may align the first hole guide and the first window trial. Further, placing the guide trial into the prosthesis may align the first hole guide with the first hole of the prosthesis.

Additionally, the method may further include discarding the guide trial after removal from the prosthesis.

Furthermore, the method may further include placing the prosthesis and insert trial into a vice.

Additionally, the method may further include removing debris from the prosthesis prior to inserting the prosthesis into the bone.

BRIEF DESCRIPTION OF THE DRAWINGS

The features, aspects, and advantages of the present invention will become better understood with regard to the following description, appended claims, and accompanying drawings in which:

DETAILED DESCRIPTION

When referring to specific directions in the following discussion of certain implantable devices, it should be understood that such directions are described with regard to the implantable device's orientation and position during exemplary application to the human body. Thus, as used herein, the term "proximal" means close to the heart and the term "distal" means more distant from the heart. Also, as used herein, the terms "about," "generally" and "substantially" are intended to mean that slight deviations from absolute are included within the scope of the term so modified.

FIGS. 1-7 illustrate an acetabular cup implant system 10 according to an embodiment of the present disclosure. System 10 generally includes a shell trial 12, liner trial 14, and a prosthesis 32. In the embodiment depicted, prosthesis 32 is an acetabular cup implant. However, it should be understood that other forms of shell prostheses, such as those configured for a glenoid cavity, may be utilized without departing from the present invention.

Figure 1:
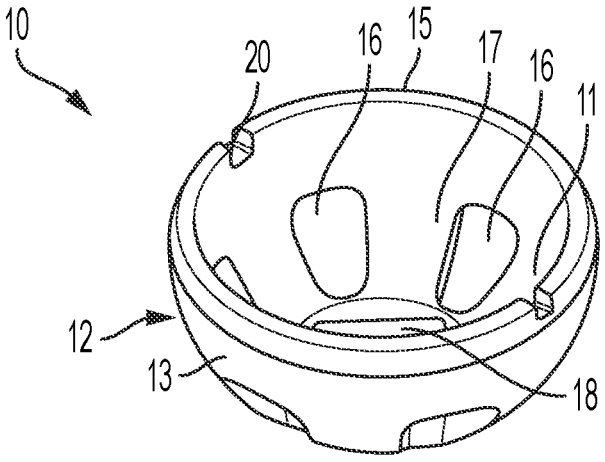
FIG. 1 is a perspective view of a window trial.
Figure 2:
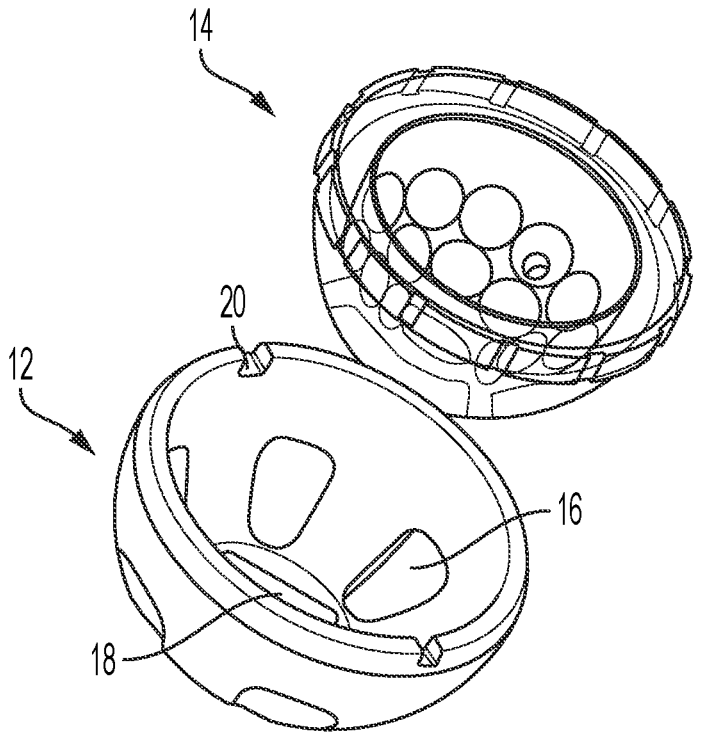
FIG. 2 is a perspective view of the window trial of FIG. 1 and a transparent liner trial.

FIGS. 1-2 depict the shell trial 12, also referred to as a window trial 12. Another exemplary shell trial can be found in U.S. Publication No. 2020/0289292, the entirety of which is hereby incorporated by reference herein. Shell trial 12 has an inner concave surface 11 and an outer convex surface 13. The inner concave surface 11 is configured to attach to liner trial 14. In this regard, inner concave surface 11 defines a cavity configured to receive liner trial 14. Shell trial 12 may include locking features (not shown) that prevent liner trial 14 from rotating or moving within the shell trial 12 when trials 12 and 14 are attached.

The shell trial 12 includes a plurality of windows 16 extending through the shell trial 12 from the inner concave surface 11 to the outer convex surface 13. As shown in FIG. 1, the windows 16 are oblong in shape. Alternatively, the windows 16 may be any suitable shape so as to allow a surgeon to see through the windows 16 to the bone beneath. The windows 16 are spaced circumferentially about a polar axis of shell trial 12. Alternatively, the windows 16 may be spaced in a different arrangement that allows a surgeon to optimally see bone through the windows 16. Between each window 16 is a bridge portion 17. The bridge portions 17 provide structural support to shell trial 12 without being too wide as to minimize the size of the window 16 and to limit the operator's ability to visualize underlying bone.

The outer convex surface 13 and the inner concave surface 11 of the shell trial 12 define a circular rim 15 therebetween. The rim 15 includes at least one notch 20. Notch 20 allows shell trial 12 to be easily attached and removed from an insertion and/or extraction tool (not shown) during operation. The notch 20 shown in FIG. 1 is rectangular in shape, but other notch shapes are envisioned, such as a V-shape, for example.

The shell trial 12 further includes a dome portion at its distal end. The inner side of the dome portion includes a cutout 18. The cutout 18 may extend partially through or completely through the wall thickness defined between the inner concave surface 11 or the outer convex surface 13. The cutout 18 may be square-shaped or another optimal shape for engaging with an inserter/impactor. The cutout 18 facilitates engagement with an inserter/impactor instrument (not shown) for press-fit insertion of shell trial 12 into bone. Cutout 18 also allows for version control without unthreading the trial 12 from the inserter/impactor.

As illustrated in FIGS. 2-5, the acetabular cup implant system includes a liner trial. The liner trial 14, as depicted, is hemispherical. However, other shapes of liner trials may also be utilized depending on the shape of the final prosthesis. The liner trial 14 includes an inner concave surface 33, an outer convex surface 19, and a rim 35 defined by the convergence of the inner concave surface 33 and outer convex surface 19. Such rim 35 defines a proximal extent of liner trial 14 and may include a collar portion 26 extending radially outwardly therefrom and may include at least one attachment feature 30. The attachment feature 30 may be configured to allow the collar 30 to form a friction fit, rotatably locking fit, snap fit, or any other type of mechanical attachment with another device. For example, as shown, the attachment feature 30 may be a projection to mate with the notch 20 of the shell trial 12, or a groove to engage with a projection extending radially inwardly from shell trail 12. As partially illustrated in FIG. 2, the collar portion 26 of the liner trial 14 may seat onto rim 15 of the shell trial 12.

Figure 3:
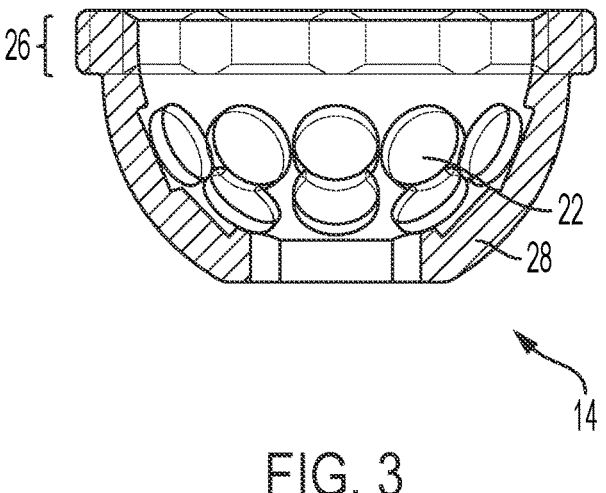
FIG. 3 is a side view of the transparent liner trial of FIG. 2.
Figure 4:
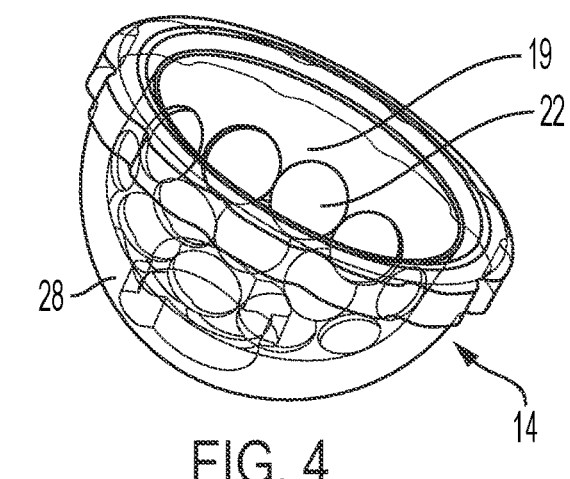
FIG. 4 is a perspective view of the transparent liner trial.
Figure 5:
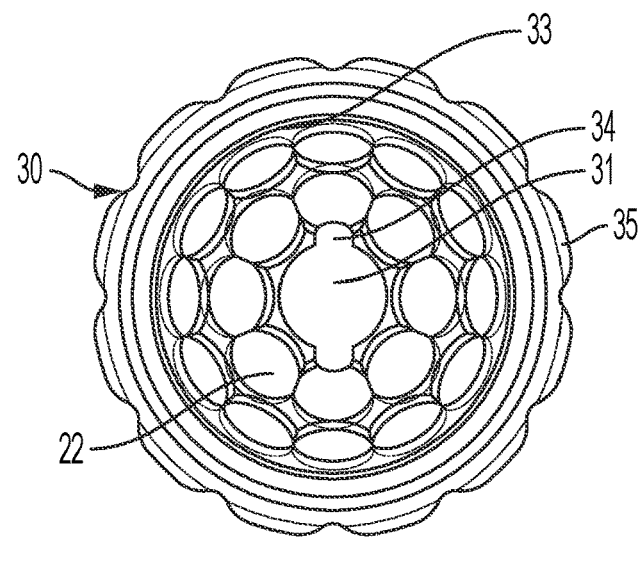
FIG. 5 is a top view of the transparent liner trial.

A dome 28 extends distally from the collar portion 26. In the embodiment depicted in FIG. 4, the dome 28 extends from the entire circumference of the rim 35, but it is envisioned that the dome 28 may extend from a portion less than 360° of the rim 35 to form a slot configured to attach with another device. The dome 28 is substantially hemispherical as depicted in FIG. 4 and may be completely enclosed, or it may define a dome hole 31 extending therethrough. As shown in FIG. 3, a distal end of dome 28 is planar. However, in other embodiments, this distal end may follow the curvature of the remainder of the dome 28. Dome hole 31 includes lobes or cut-outs 34 that are oriented 180 degrees relative to each other. Such lobes act as keys to set the orientation of liner. Alternatively, dome hole 31 may be threaded to allow the liner trial 14 to threadably attach to various devices, such as an inserter instrument (not shown). Also, the dome hole 31 may include any type and number of attachment features, such as snap fits, rotatable locking fits, or other attachment types known in the art.

The liner trial 14 is preferably transparent. It may be formed of any type of material including those that are transparent. For example, depending on the manufacturing method used, materials such as acrylonitrile butadiene styrene (ABS), Polylactic acid (PLA), ABS with additives to allow transparency, Poly(methyl methacrylate) PMMA, Polycarbonate (PC), Polyethylene terephthalate glycol (PETG), UV, and stereolithography (SLA) materials in conjunction with a transparent resin may be used. The transparency allows a surgeon to see through the liner trial 14 and through the windows 16 of a shell trial 12 when the liner trial 14 is placed into an acetabulum. The surgeon can then manipulate the liner trial 14 in such a manner that allows the surgeon to at least view windows 16 of shell trial and perhaps even the underlying bone through liner trial 14. This allows the surgeon to drill through liner trial 14 into optimal regions of bone for receiving a bone screw, as described in more detail below.

The liner trial 14 further comprises a plurality of hole guides 22 arrayed along inner concave surface 33. The hole guides 22 may be located directly adjacent one another to cover a maximum amount of surface area of inner concave surface 33. In another embodiment, the hole guides 22 may be staggered relative to each other or spaced apart in a plurality of patterns. In some embodiments, hole guides 22 may be spaced apart from one another, such as a distance of at least half the diameter of each hole guide 22. The hole guides 22 are preferably circular to allow for a drill bit to be inserted therein without slipping and to help the surgeon visualize the extent of the material that will be removed by the drill bit. Each hole guide 22 may be recessed into the wall portion defined between the inner concave surface 33 and outer convex surface 19 such that each hole guide 22 stops short of extending through the entire thickness of trial 14. As described below, a surgeon may drill through a desired hole guide 22. Hole guides 22 that do not extend through the thickness of trial 14 helps the surgeon quickly and easily identify which hole guides 22 were used so that the ones that were used can act as a template to drill out prosthesis 32. However, it should be understood that in some embodiments of liner trial 14, hole guides 22 can extend through the entire thickness thereof but, in such circumstance, would generally require some sort of marking or indicator be used to identify which hole guide 22 was used by the surgeon.

Figure 6:
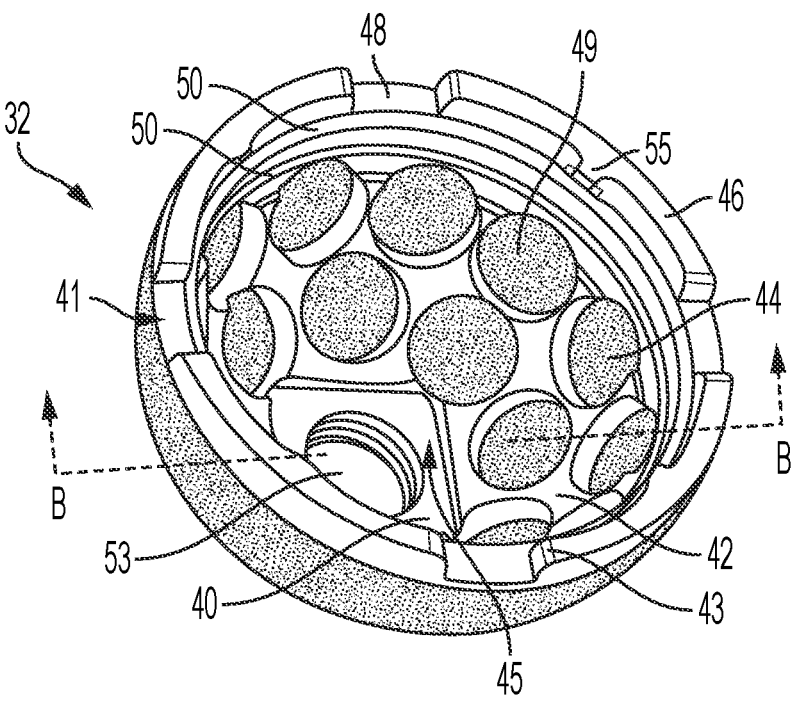
FIG. 6 is a perspective view of an acetabular cup implant from a proximal direction.
Figure 7:
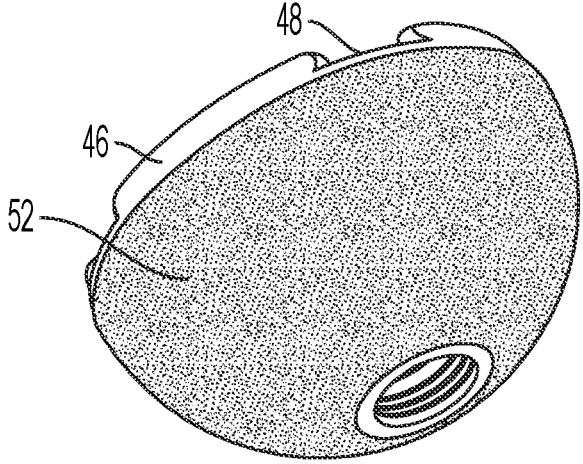
FIG. 7 is a perspective view of the acetabular cup implant of FIG. 6 from a distal direction.

FIGS. 6-7 depict an acetabular cup implant 32. Like the trials, the acetabular cup implant 32 is substantially hemispherical in nature. The acetabular cup implant 32 includes a solid inner portion 41 and a porous structure 52 at its exterior. The solid inner portion 41 includes a concave inner surface 42, a convex outer surface, and a rim 43 defined therebetween. The rim 43 includes a plurality of attachment/engagement features in the form of projections 46 and notches 48 for engagement with an inserter/impactor instrument. Rim 43 includes further attachment/engagement features in the form of inwardly extending projections or tabs (55) which are configured to be received within grooves 30 of liner trial 14. It is envisioned that the attachment features 46, 48, 55 may include any number and any type of attachment feature known in the art.

The solid inner portion 41 includes a plurality of preformed holes 49. The holes 49 may be spaced directly adjacent one another so that the bridge portion of material between each hole 49 is as minimal as possible while still providing sufficient structural support. In this regard, holes 49 generally mirror the pattern of hole guides 22 found in liner trial 14. The holes 49 preferably extend entirely through the solid inner portion 41 so that an operator does not have to drill through solid metal in the operating room. However, it should be understood that holes 49 may extend only partially through the solid inner portion 41 similar to hole guides 22. Having a maximum number of predrilled holes 49 is preferable as it allows for the most orientations of bone screws into the acetabulum and the best chance of properly securing the acetabular cup implant 32 to the acetabulum to the healthiest bone.

The holes 49 of the acetabular cup implant 32 may be dimensioned according to the size of appropriate screws. The diameter of the holes 49 should be smaller than the diameter of the screw head (not shown) to provide a surface for the screw head to abut and counteract the driving force as the screw is driven through the implant 32 into a bone. The acetabular cup implant 32 may also include screw-retaining features (not shown) for each hole 49. In such embodiments, screw retaining features can be back-out prevention features, such as retaining rings, lock washers, and the like. Alternatively, the holes 49 may be made of a softer material than the surrounding solid inner portion 41. This softer material allows for the screw heads to bite into the softer material and prevents the screw from backing out. The bridge portion of the solid inner portion 41 should be wide enough to allow for adjacent screw heads to abut the bridge portion without contacting each other. Although the embodiment shown in FIG. 6 depicts holes 49 with a central axis perpendicular to the solid inner portion 41, the holes 49 could be formed at any orientation relative to the solid inner portion 41 to allow for a variety of screw angles. In one embodiment, the holes 49 may include a ramp portion (not shown) formed by a countersink bit. This ramp portion may allow a polyaxial screw, such as a screw with a spherical head, to be used therewithin so the screw could be driven through the solid inner portion 41 along multiple axes relative to the solid inner portion 41. In an embodiment with ramp portions in the holes 49, the bridge portions should be wide enough to accommodate a screw head sitting at any angle relative to the hole 49 without abutting another screw head in an adjacent hole 49. It is also envisioned in a further embodiment that holes 49 can have any size chamfer or fillet along their edges to accept different types of screws.

As depicted in FIG. 6, the concave inner surface 42 of the solid inner portion 41 may include a plurality of annular ridges 50 located circumferentially and distally from the rim 43. The ridges 50 may be dimensioned as to allow any size of a shell trial 12 or liner trail 14 to couple therewithin. The ridges 50 may be located proximal to the holes 49, distal to the holes 49, or spaced between the holes 49. As mentioned above, concave inner surface 42 may further include tabs 55 to assist in limiting rotation of the liner trial 14 when the liner trial 14 is placed within the concave inner surface 42 of the acetabular cup implant 32. The tabs may extend proximally from the concave inner surface 42 or may have another arrangement commonly used to prevent rotation.

The dome portion 45 of the solid inner portion 41 also includes a threaded bore 53 for connection to an inserter/impactor instrument and a vice, as described below. As shown in FIG. 6, a cutout or indentation 40 surrounds bore 53. The cutout 40 may be any shape but is preferably square-shaped. Further locking features and attachment features not shown may also be included.

Figure 8:
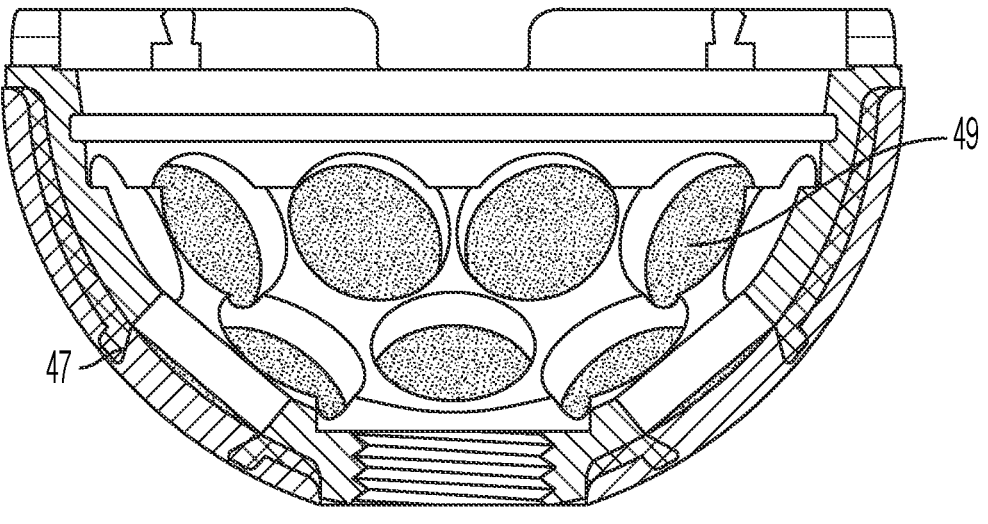
FIG. 8 is a side cross-sectional view of the acetabular cup implant of FIG. 6 taken along line B-B.

A porous structure 52 encapsulates the outer convex side of the acetabular cup implant 32. The solid inner portion 41 may include a chamfer 47 on its outer convex side. As depicted in FIG. 8, the porous structure 52 is sunken beneath the chamfer 47 such that the porous structure 52 does not contact a polymer liner when a polymer liner is used in conjunction with the acetabular cup implant 32. Further, holes can be drilled through the porous structure 52 to align with the holes 49 of the acetabular cup implant 32. The chamfer 47 may be any size as to seat the porous structure 52.

The porous structure 52 may be a porous coating, such as Titanium Plasma Spray (TPS), Hydroxyapatite (HA), a spherical bead coating, or any combination thereof, that is added to the outside of the solid inner portion 41, or it may be a separate structure altogether that is then attached to the solid inner portion 41. If the porous structure 52 is a separate structure, it may be attached using adhesives, fasteners, friction fits, welding or other connection methods commonly known in the art. However, porous structure 52 is preferably made via an additive manufacturing process and integrated into the solid inner portion 41, as described below.

Porosity is generally a measure of a structure's empty space relative to the total space occupied by the structure. More specifically porosity is characterized by the equation $\Psi = V_V / V_T$ where $\Psi$ is the porosity, $V_V$ is the volume of empty space or void-space, and $V_T$ is the total volume including the volume of materials defining the void-space and the void-space itself. In the embodiment depicted in FIG. 6, the porosity of the porous structure 52 may be about 10% to 90% with an average pore size of between 20-1000 microns. However, porous structure 52 preferably includes a pore size of between 100 and 700 microns with a mean pore size of 400 to 500 microns and a mean porosity of 55% to 65%.

As discussed above, porosity is generally a measure of a material's empty space relative to the total space occupied by the material. In contrast, solid inner portion 41 does not have a porosity or has a porosity of substantially zero. In this regard, while solid inner portion 41 is considered a solid structure, it is recognized that structures that are seemingly non-porous, at least to the naked eye, may have a porosity on a very small scale. Indeed, structures that are manufactured using the additive manufacturing technique of selective laser sintering (discussed below) often have an inherent porosity to the material. Thus, as used herein, the terms non-porous and solid mean a porosity so small or so close to zero as to prohibit bone growth therein.

The exemplary implants described herein may be formed layer-by-layer using an additive layer manufacturing (ALM), i.e., 3D printing, process so no separate connection mechanism is necessary to bring together any of the components of such implants. In some examples, ALM processes are powder-bed based and involve one or more of selective laser sintering (SLS), selective laser melting (SLM), and electron beam melting (EBM), as disclosed in U.S. Pat. Nos. 7,537,664; 8,728,387; 9,180,010; and 9,456,901 as well as U.S. Patent Publication No. 2006/0147332, each of which is hereby incorporated by reference in their entireties herein. Other methods of ALM, which can be used to form the herein described implants, include stereolithography (SLA), fused deposition modeling (FDM), and continuous liquid interface production (CLIP).

When employing powder-bed based technologies, articles are produced in layer-wise fashion according to a predetermined digital model of such articles by heating, e.g., using a laser or an electron beam, multiple layers of powder, which preferably may be a metallic powder, that are dispensed one layer at a time. The powder is sintered in the case of SLS technology and melted in the case of SLM technology, by the application of laser energy that is directed in raster-scan fashion to portions of the powder layer corresponding to a cross section of the article. After the sintering or melting of the powder on one particular layer, an additional layer of powder is dispensed, and the process repeated, with sintering or melting taking place between the current layer and the previously laid layers until the article is complete. The powder layers similarly may be heated with EBM technology. Additive manufacturing techniques such as the ALM processes described above may be employed to form the solid and porous layers and any other components, as applicable. In some instances, materials for one layer may be different than the materials for successive layers. This process allows for porous portions to extend full thickness through a particular structure.

Each of solid and porous layers of the above described implants may be constructed from biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium, or biocompatible polymers, such as but not limited to any one of or any combination of polyethylene (PE) and variations thereof, polyetheretherketone (PEEK), polyether-ketone (PEK), acrylonitrile butadiene styrene (ABS), silicone, and cross-linked polymers. In some arrangements, the implants described herein may be made of certain other materials such as but not limited to bioabsorbable glass, ceramics, and biological active materials including collagen/cell matrices. In some arrangements, the implant may be made of a combination of any of these metals, polymers, and other materials. All constituent porous and solid portions of the above-described implants may be a common material, such as one of those listed above, or different materials can be employed for each part. Particular combinations of materials and their use for specific parts of herein described implants are a matter of design choice and may include the combination of different metals, different polymers, or metals combined with polymers. For example, the solid portions of the herein described implants can be made from a metal while the porous portions may be made from a polymer.

Figure 9:
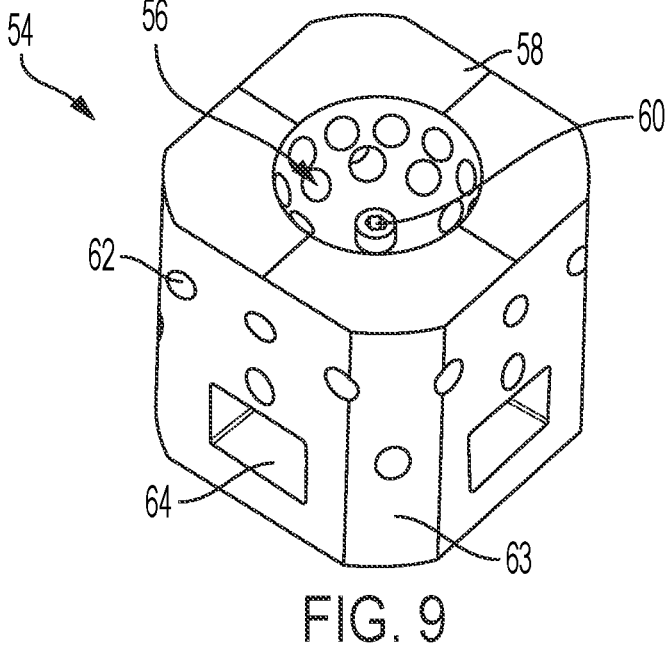
FIG. 9 is a perspective view of a vice, according to one embodiment.

A vice 54 is depicted in FIG. 9. The vice 54 may be used in an operating room while being affixed to a back table. In one embodiment, the vice 54 includes a hemispherical opening 56 configured to receive the acetabular cup implant 32. The hemispherical opening 56 includes a plurality of predrilled holes 62 that align with the plurality of holes 49 in the acetabular cup implant 32. The predrilled holes 62 preferably align with the same axes created by the holes 49 of the acetabular cup implant 32 regardless of whether the implant holes 49 are configured for polyaxial screws or not.

The hemispherical opening 56 includes a dome with an alignment plug 60 located therein. The alignment plug 60 is configured to locate any one of the acetabular cup implant 32, the liner trial 14, and the window trial 12, or any combination thereof. The alignment plug 60 may have corresponding threads as to engage with the threaded portions of the acetabular cup implant 32. The hemispherical opening 56 may be smooth or it may be textured to allow for an enhanced grip between the vice 54 and the any device being placed within the vice 54. The vice 54 further has alignment markings 58 to assist with aligning any number of features of a device with the vice 54. Chamfers 63 may be provided along the corners of the vice 54 to allow for less material bulk.

In the embodiments shown in FIG. 9, the vice 54 includes four slots 64 for engaging with a clamp. The clamp may be a C-clamp, spring clamp, or any other clamp known in the art. The clamp allows the vice 54 to be fixed to a table to allow for a stable working area for an operator. The slots 64 are rectangular as shown in FIG. 9, but they may be any shape configured to attach with a clamp. Further, although the embodiment depicted shows four slots 64, any number of slots 64 may be located in the vice 54. Other fixation methods than clamps may also be used to secure the vice to a surface.

Figures 11, 12:
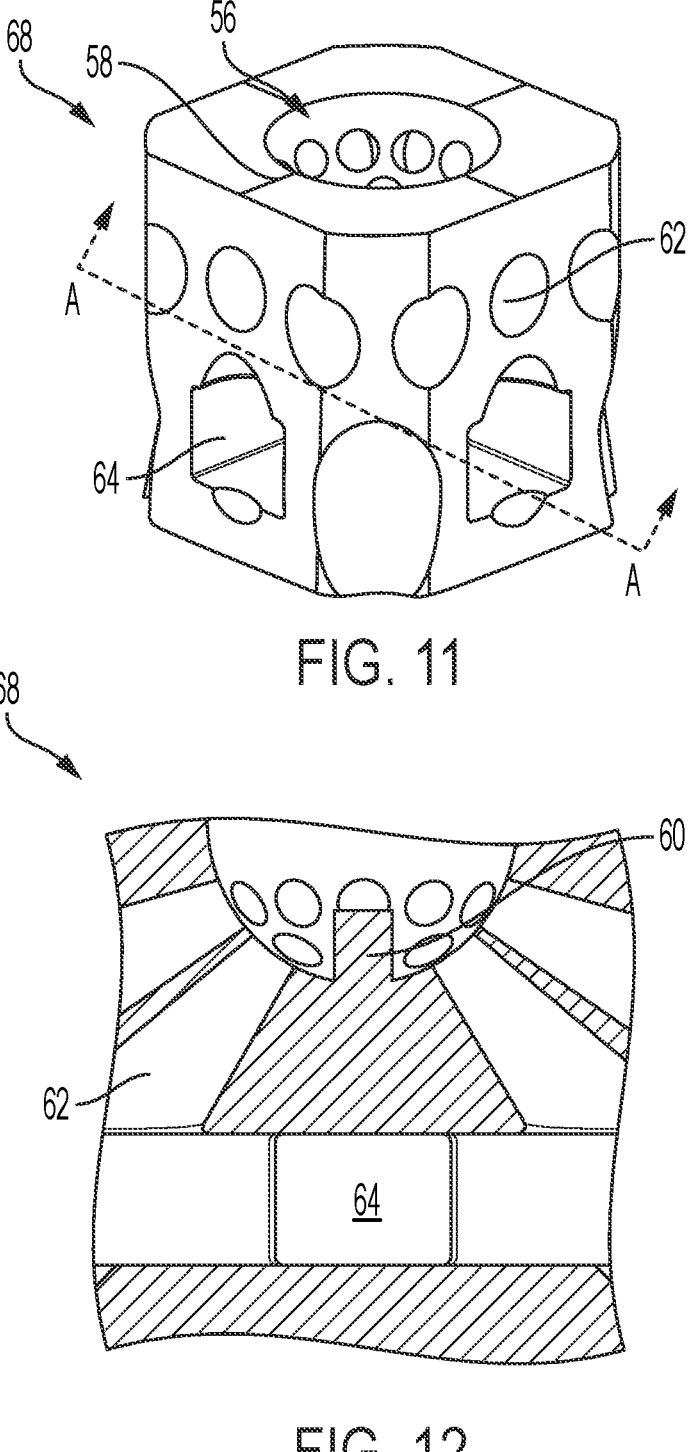
FIG. 11 is a perspective view of another vice, according to one embodiment.
FIG. 12 is a cross-sectional view of the vice of FIG. 11, taken along A-A.

In an alternative embodiment of a vice 66 shown in FIG. 11, the vice 68 may have a pattern of predrilled conical holes 62. The conical holes 62 allow for increased angulation when a user drills through the vice 68 into the acetabular cup implant 32. This configuration may be preferable if unique angles are needed for a specific patient or if polyaxial screws are used within the acetabular cup implant 32. This configuration may also have an alignment plug 60 and alignment markings 58 for positioning the acetabular cup implant 32 within the vice 68.

Figure 10:
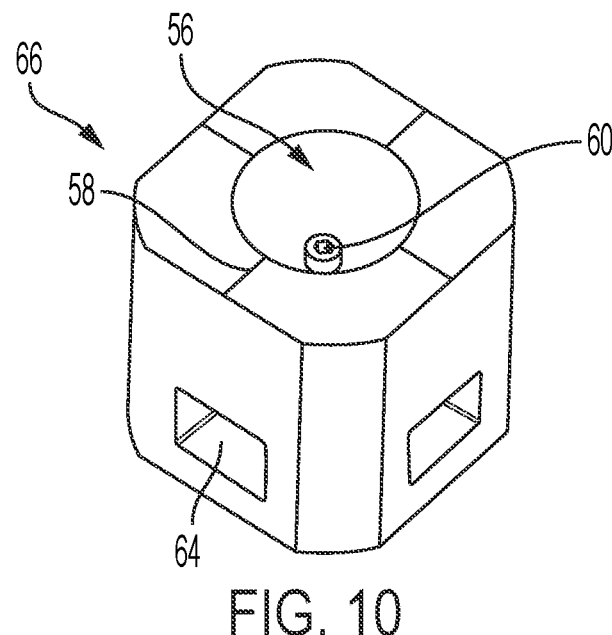
FIG. 10 is a perspective view of another vice, according to one embodiment.

In yet another embodiment of vice 66 shown in FIG. 10, no predrilled holes are provided. Rather, the vice 66 is made from a disposable material that allows an operator to easily drill through the vice 66 into the acetabular cup implant 32 an any desired angle. This material preferably limits burrs and other scrap material from falling into the acetabular cup implant 32. This configuration may also have an alignment plug 60 and alignment markings 58 for positioning the acetabular cup implant 32 within the vice 66. It is also envisioned that an operator could first drill through the acetabular cup implant 32 and then into the vice 66.

Figure 16:
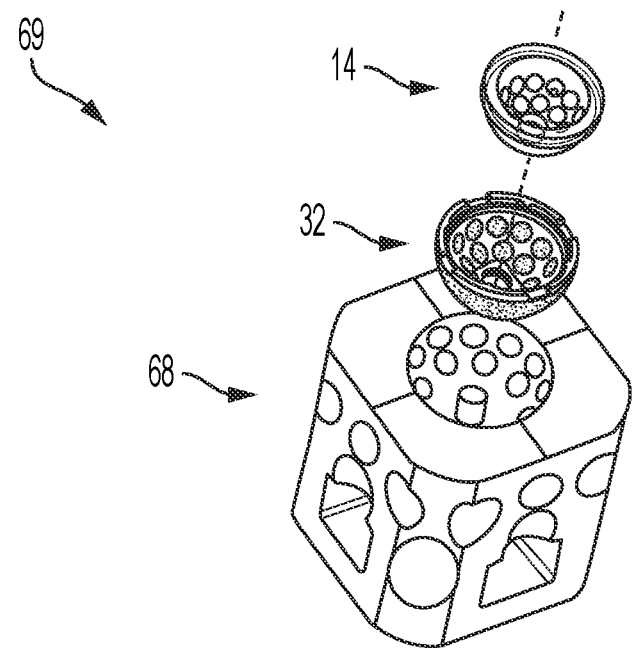
FIG. 16 is a perspective view of the vice of FIG. 11 receiving both the acetabular cup implant of FIG. 6 and the transparent liner trial of FIG. 3.
Figure 17:
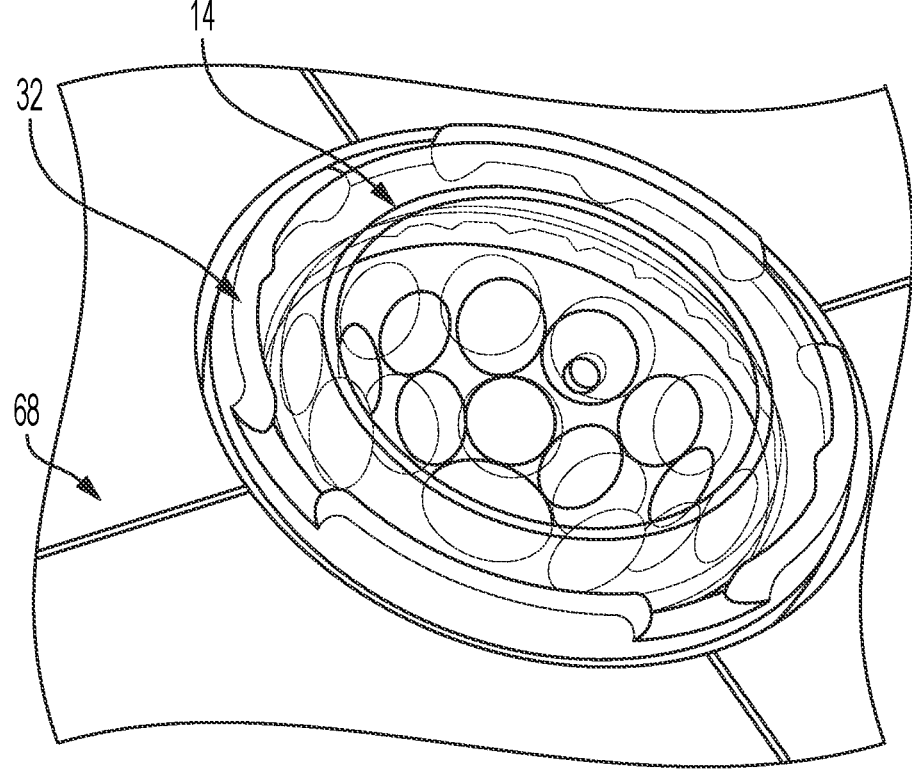
FIG. 17 is a perspective view of the vice of FIG. 11, the acetabular cup implant of FIG. 6, and the transparent liner trial of FIG. 3, where the transparent liner trial is seated within the acetabular cup implant and the acetabular cup implant is seated within the vice.

In an embodiment illustrated in FIGS. 1 and 16, an acetabular cup preparation system 69 for preparing an acetabular cup prosthesis for implantation is provided and generally includes window trial 12 (not shown in FIG. 16), liner trial 14, and acetabular cup implant 32 The window trial 12 engages with an acetabulum and the liner trial 14 is dropped into the window trial 12. The liner trial 14 can be placed within the acetabular cup implant 32 to assist with aligning the hole guides 22 of the liner trial 14 with the holes 49 of the acetabular cup implant 32. Each of the liner trial 14 and acetabular cup implant 32 can be secured to a vice 54. The vice 54 may include a pattern of predrilled holes or it may comprise a surface that allows an operator to drill through the vice into the acetabular cup implant 32.

A method for implanting a prosthesis into a bone cavity is provided. In one embodiment, the bone cavity is an acetabulum, and the prosthesis is an acetabular cup implant 32. However, this method may be applied to other prosthetic implants located in other bone cavities throughout the body.

The method first comprises inserting a window trial 12 into the bone cavity. The window trial 12 has a plurality of windows 16 that allow a surgeon to see bone behind the window trial 12. The surgeon can locate bone structure that is strong and ideal for drilling. Once the windows 16 are aligned with bone configured to be drilled into, the surgeon may insert the transparent liner trial 14 into the window trial 12.

Due to the transparency of the liner trial 14, a surgeon may see through the liner trial 14 at the window trial 12 and bone underneath. The surgeon may then rotate and lock the liner trial 14 relative to the window trial. The surgeon then has several options. The surgeon may drill a hole through the hole guides 22 and the window 16 into the bone or may mark the location of the aligning hole guide 22 using a punch, surgical marker, or other marking device. Once the appropriate hole guides 22 of the liner trial 14 have been identified, the surgeon may first remove the liner trial 14 and then the window trial 12 or may remove both trials concurrently. However, it should be noted that, before the trials are removed and preferably before any marking or drilling is performed, such trials 12, 14 may be used to articulate with a proximal femoral trial in order to test the fit and orientation thereof.

Once the transparent liner trial 14 has been removed, an operator may place the liner trial 14 into the acetabular cup implant 32. Preferably, this insertion takes place with the assistance of a vice, such as vices 54, 66, and 68, located at a back table in the operating room. Alternatively, the vice could be located elsewhere, or the operator could couple the liner trial 14 and the acetabular cup implant 32 together without using a vice.

In an embodiment where a vice is provided such as that depicted in FIG. 11, an operator first provides an acetabular cup implant 32 configured to engage with the vice. The operator rotates the acetabular cup implant 32 to engage its threads with the corresponding threads of the vice. This rotation translates the acetabular cup implant 32 into the corresponding hemispherical opening 56 located in the proximal end of the vice 68. Once the acetabular cup implant 32 is seated in the hemispherical opening 56, a locking feature may prevent further rotation of the acetabular cup implant 32 relative to the vice.

An operator then provides the liner trial 14, described above. Preferably, the liner trial 14 will be provided with marked or predrilled hole guides 22. The operator then drops the liner trial 14 into acetabular cup implant 32 and secures its orientation via the locking feature may to prevent further rotation of the liner trial 14 relative to the acetabular cup implant 32 or the vice 68 and to ensure the proper orientation. This locking feature may be a tab configured to engage with a groove or any other type of locking feature known in the art.

Once the operator is satisfied with the alignment of the holes 49 of the acetabular cup implant 32 and the holes of the liner trial 14, the operator can prepare to drill through the acetabular cup implant 32. The operator may select an appropriate drill bit corresponding to the size of the screw being used to secure the prosthetic. The operator then aligns the drill bit with the central axis of the preferred predrilled vice hole and drives the drill bit through each of the liner trial 14, acetabular cup implant 32, and vice. After drilling through each hole required, the operator should ensure that any burrs or other undesired material is removed from the prosthesis.

After each hole has been drilled and deburred, the operator may then remove the liner trial 14 from the acetabular cup implant 32 and vice. First, the locking feature securing the liner trial 14 is detached. Second, the operator translates the liner trial 14 proximally out of prosthesis 32. Once the liner trial 14 is removed, it may be discarded. A similar process is used to remove the acetabular cup implant 32. First, any locking features used to lock the rotation of the acetabular cup implant 32 are detached. Second, the operator rotates the acetabular cup implant 32 in a loosening direction to translate the acetabular cup implant 32 proximally. Once the acetabular cup implant 32 has been removed, it may be prepared for implantation into the bone cavity.

Figures 13, 14, 15:
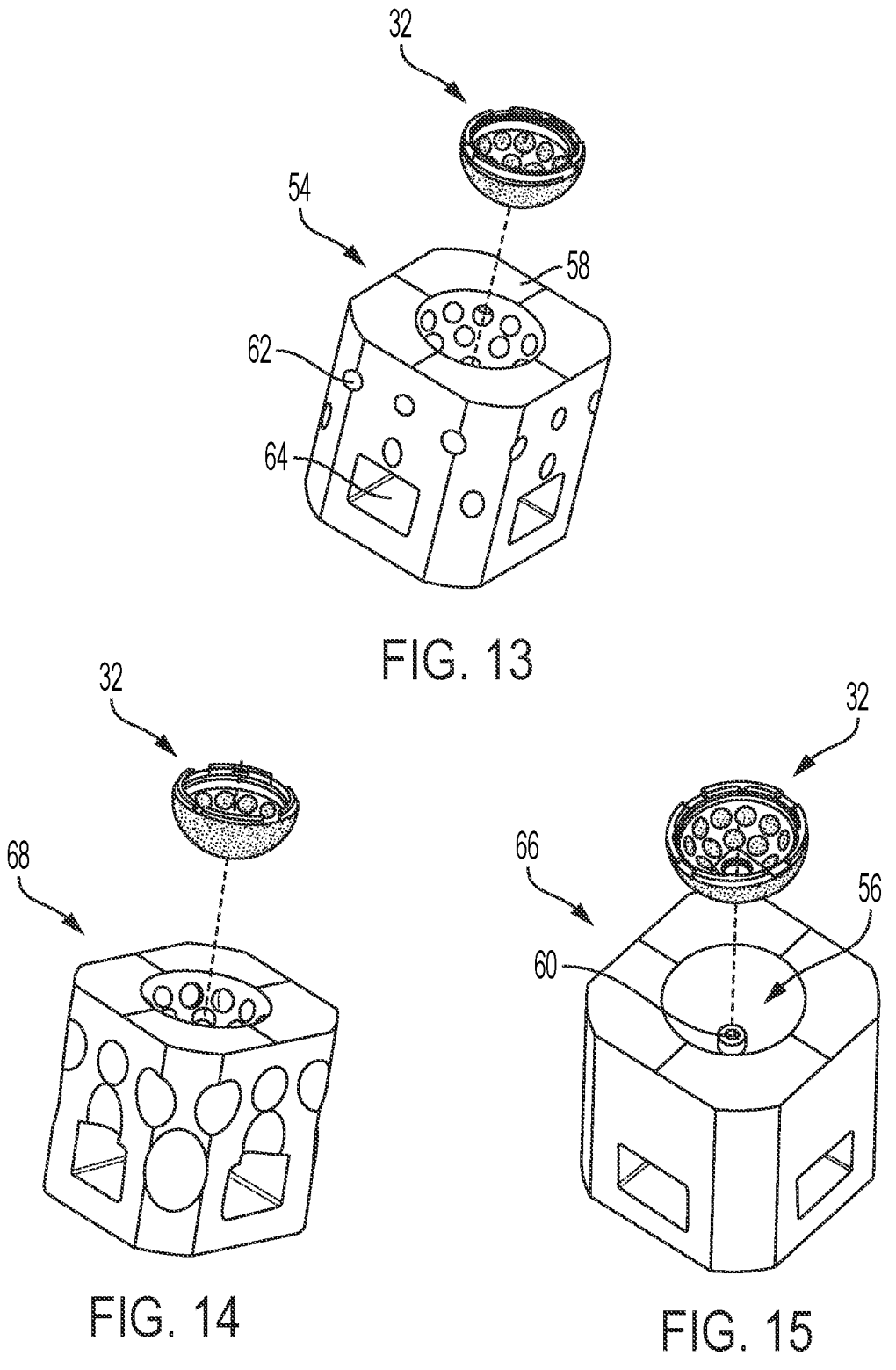
FIG. 13 is a perspective view of the vice of FIG. 9 receiving the acetabular cup implant of FIG. 6.
FIG. 14 is a perspective view of the vice of FIG. 11 receiving the acetabular cup implant of FIG. 6.
FIG. 15 is a perspective view of the vice of FIG. 10 receiving the acetabular cup implant of FIG. 6.

In an alternative method embodiment shown in FIG. 15 and using a vice 66 depicted in FIG. 10, each step remains the same as the method above, except for the drilling step. Because the vice 66 has no predrilled holes, an operator ends up drilling into the substrate of vice 66 instead of a pre-formed hole therein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical guide system comprising:
a shell trial having a convex side configured to engage an acetabulum, a concave side forming a cavity therein, and windows extending through the convex and concave sides for viewing bone;
a liner trial having a convex side configured to be received within the cavity of the concave side of the shell trial, and a concave side with recessed hole guides therein, wherein more than one of the hole guides align with the windows of the shell trial when the liner trial is received therein; and
an acetabular cup implant having a convex side configured to engage an acetabulum, a concave side, and a thickness extending between the concave and convex sides, the concave side defining a cavity configured to receive the liner trial and having a plurality of holes extending therein and at least partially into the thickness, wherein the recessed hole guides and holes of the acetabular cup align when the liner trial is received within the cavity of the acetabular cup implant.

2. The surgical guide system of claim 1, wherein the recessed hole guides of the liner trial are located adjacent one another and arrayed about a polar axis of the liner trial.

3. The surgical guide system of claim 1, wherein the plurality of holes in the acetabular cup are positioned adjacent one another and arrayed about a polar axis of the acetabular cup.

4. The surgical guide system of claim 3, wherein:
the acetabular cup includes a rim defined by a convergence of the concave and convex sides thereof, the rim including a first engagement feature,
the liner trial includes a rim defined by a convergence of the concave and convex sides thereof, the rim of the liner trial including a second engagement feature,
the recessed hole guides of the liner trial align with the plurality of holes in the acetabular cup when the first and second engagement features engage with each other.

5. The surgical guide system of claim 1, further comprising a vice having a concave cavity for receipt of the acetabular cup implant and a plurality of cylindrical or conical channels in communication with the concave cavity, the cylindrical or conical channels aligning with the plurality of holes of the acetabular cup when received within the concave cavity.

6. The surgical guide system of claim 1, wherein the acetabular cup implant has a porous structure on the convex side such that it occludes the plurality of holes.

7. The surgical guide system of claim 1, wherein the convex side of the acetabular is formed from a solid metal material which defines each of the plurality of holes in the acetabular cup.

8. A liner trial for visualizing the placement of a bone screw comprising:
a convex bone facing side;
a concave visualization side opposite the bone facing side and defining a thickness between the bone facing side and visualization side; and
hole guides extending radially outwardly into the visualization side and partially into the thickness.

9. The liner trial of claim 8, wherein the liner trial is transparent.

10. The liner trial of claim 8, wherein the hole guides are spaced adjacent one another to cover a maximum amount of surface area on the concave visualization side.

11. The liner trial of claim 8, further comprising an insertion feature having a threaded bore configured to engage with a corresponding threaded portion of an attachment feature.

12. The liner trial of claim 11, wherein the attachment feature is at least one of a window trial, vice, and implant.

13. The liner trial of claim 8, wherein the insertion feature is configured to frictionally engage with at least one of a window trial, vice, and implant.

14. A method of implanting a prosthesis into a bone cavity comprising:

inserting a window trial with a first window into a bone;

placing a guide trial with a first hole guide into the window trial;

drilling through the first hole guide and the first window into the bone;

removing the guide trial from the bone;

placing the guide trial into a prosthesis, the prosthesis having an inner surface with a plurality of holes and a porous outer surface occluding the holes;

drilling through the first guide hole, a first hole of the plurality of holes in the inner surface of the prosthesis, and the porous outer surface;

inserting the prosthesis into bone; and inserting a bone screw through the first hole in the prosthesis and into the bone.

15. The method of claim 14, wherein the bone structure is an acetabulum.

16. The method of claim 14, further comprising aligning the first window of the window trial with a region of relatively dense bone.

17. The method of claim 14, further comprising:

drilling through a second hole guide and second window into the bone, drilling through the second guide hole, a second hole of the plurality of holes in the inner surface of the prosthesis and the porous outer surface, and inserting a bone screw through the second hole in the prosthesis and into the bone.

18. The method of claim 14, wherein placing the guide trial into the window trial aligns the first hole guide and first window trial, and placing the guide trial into the prosthesis aligns the first hole guide with the first hole of the prosthesis.

19. The method of claim 14, further comprising discarding the guide trial after removal from the prosthesis.

20. The method of claim 14, further comprising placing the prosthesis and insert trial into a vice.

* * * * *